US012127867B2

(12) United States Patent
Uzbelger Feldman

(10) Patent No.: US 12,127,867 B2
(45) Date of Patent: *Oct. 29, 2024

(54) LOW-DOSE X-RAY IMAGING SYSTEM

(71) Applicant: REAL TIME IMAGING TECHNOLOGIES, LLC, Charlotte, NC (US)

(72) Inventor: Daniel Uzbelger Feldman, Charlotte, NC (US)

(73) Assignee: REAL TIME IMAGING TECHNOLOGIES, LLC, Charlotte, NC (US)

( * ) Notice: Subject to any disclaimer, the term of this patent is extended or adjusted under 35 U.S.C. 154(b) by 175 days.

This patent is subject to a terminal disclaimer.

(21) Appl. No.: 18/099,971

(22) Filed: Jan. 22, 2023

(65) Prior Publication Data
US 2023/0157653 A1 May 25, 2023

Related U.S. Application Data

(63) Continuation of application No. 17/106,870, filed on Nov. 30, 2020, now Pat. No. 11,559,268, which is a
(Continued)

(51) Int. Cl.
*A61B 6/00* (2024.01)
*A61B 6/02* (2006.01)
(Continued)

(52) U.S. Cl.
CPC ............ *A61B 6/4216* (2013.01); *A61B 6/022* (2013.01); *A61B 6/025* (2013.01); *A61B 6/032* (2013.01);
(Continued)

(58) Field of Classification Search
CPC .......... A61B 6/06; A61B 6/14; A61B 6/1415; A61B 6/42; A61B 6/4205; A61B 6/4258; A61B 6/4291; A61B 6/52; A61B 6/5211; A61B 6/4216; A61B 6/037; A61B 6/032; A61B 6/4085; A61B 6/025; A61B 6/5258; A61B 6/022; A61B 6/463; A61B 6/4233; A61B 6/487; A61B 6/5205; A61B 6/4241;
(Continued)

(56) References Cited

U.S. PATENT DOCUMENTS 6,543,936 B2  4/2003  Uzbelger Feldman
8,430,563 B2  4/2013  Uzbelger Feldman
(Continued)

*Primary Examiner* — Jurie Yun
(74) *Attorney, Agent, or Firm* — TILLMAN WRIGHT, PLLC; Chad D. Tillman

(57) ABSTRACT

A back illuminated sensor is included as a collector component of a detector for use in intraoral and extraoral 2D and 3D dental radiography, digital tomosynthesis, photon-counting computed tomography, positron emission tomography (PET), and single-photon emission computed tomography (SPECT). The disclosed imaging method includes one or more intraoral or extraoral emitters for emitting a low-dose gamma ray or x-ray beam through an examination area; and one or more intraoral or extraoral detectors for receiving the beam, each detector including a back illuminated sensor. Within the detector, the beam is converted into light and then focused and collected at a photocathode layer without passing through the wiring layer of the back illuminated sensor.

20 Claims, 4 Drawing Sheets

Related U.S. Application Data continuation-in-part of application No. 15/647,239, filed on Jul. 11, 2017, now Pat. No. 10,849,586, which is a continuation of application No. PCT/US2016/013024, filed on Jan. 12, 2016.

(60) Provisional application No. 62/102,216, filed on Jan. 12, 2015.

(51) Int. Cl.
| | |
|---|---|
| *A61B 6/03* | (2006.01) |
| *A61B 6/40* | (2024.01) |
| *A61B 6/42* | (2024.01) |
| *A61B 6/46* | (2024.01) |
| *A61B 6/51* | (2024.01) |

(52) U.S. Cl.
CPC ............ *A61B 6/037* (2013.01); *A61B 6/4085* (2013.01); *A61B 6/4233* (2013.01); *A61B 6/4241* (2013.01); *A61B 6/463* (2013.01); *A61B 6/487* (2013.01); *A61B 6/51* (2024.01); *A61B 6/5205* (2013.01); *A61B 6/5258* (2013.01)

(58) Field of Classification Search
CPC .......... A61B 6/51; G01T 1/16; G01T 1/1641; G01T 1/1644; G01T 1/24; G01T 1/244; G01T 1/247; G01T 1/29; G01T 1/2928; G01T 1/2985; H04N 5/30; H04N 5/32; H04N 5/321; H04N 5/335; H04N 5/372; H04N 5/374; H01L 27/14; H01L 27/144; H01L 27/146; H01L 27/14601; H01L 27/14603; H01L 27/14618; H01L 27/14625; H01L 27/14627; H01L 27/14627; H01L 27/14464; H01L 27/14643; H01L 27/14658; H01L 27/14676; H01L 27/148; H01L 27/14806; H01L 27/14812; H01L 27/14893
See application file for complete search history.

(56) References Cited

U.S. PATENT DOCUMENTS

| | | |
|---|---|---|
| 10,849,586 B2 | 12/2020 | Uzbelger Feldman |
| 10,898,070 B2 | 1/2021 | Uzbelger Feldman |
| 11,559,268 B2 | 1/2023 | Uzbelger Feldman |
| 11,786,190 B2 | 10/2023 | Kim et al. |
| 2012/0213330 A1 | 8/2012 | Uzbelger Feldman |
| 2023/0139873 A1 | 5/2023 | Loi et al. |

LOW-DOSE X-RAY IMAGING SYSTEM

CROSS-REFERENCE TO RELATED APPLICATION

The present application is a U.S. continuation of, and claims priority under 35 U.S.C. § 120 to, U.S. nonprovisional patent application Ser. No. 17/106,870, filed Nov. 30, 2020, which '870 application is a continuation-in-part of, and claims priority under § 120 to, U.S. nonprovisional patent application Ser. No. 15/647,239, filed Jul. 11, 2017, which '239 application and any publication thereof or patent issuing therefrom are hereby incorporated herein by reference, and which '239 application is a U.S. continuation of, and claims priority under § 120 to, international patent application PCT/US16/13024, filed Jan. 12, 2016, and which '024 international application is a U.S. nonprovisional patent application of, and claims priority under 35 U.S.C. § 119 to, U.S. provisional patent application 62/102,216, filed Jan. 12, 2015, which '216 application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to low-dose x-ray imaging apparatus and methods. Preferred embodiments relate to such apparatus and methods used in the context of intraoral and extraoral 2D and 3D dental imaging, digital tomosynthesis, photon-counting computed tomography, positron emission tomography (PET), and single-photon emission computed tomography (SPECT).

Many intraoral and extraoral dental imaging apparatus and methods are known. Current dental x-ray imaging, digital tomosynthesis, photon-counting computed tomography and PET/SPECT scan devices comprise front illuminated sensors. A traditional front-illuminated sensor is constructed in a fashion similar to the human eye, with a pixel gate and a digital matrix at the front and photodetectors at the back. This traditional orientation of the sensor places the active matrix of the digital image sensor—a matrix of individual picture elements—on its front surface and simplifies manufacturing. The matrix and its wiring, however, reflect some of the light, and thus the photocathode layer can only receive the remainder of the incoming light; the reflection reduces the signal that is available to be captured resulting in a decrease in sensor's quantum efficiency (QE). Consequently, front illuminated systems require increased radiation doses and large pixel sizes in order to gather enough light to produce an image. Patent references disclosing dental and medical imaging apparatus and methods following these principles include U.S. Pat. Nos. 4,057,727; 5,434,418; 5,834,782; 6,972,411; 7,016,461; 7,136,452; 7,197,109; 7,319,736; 7,322,746; 7,323,697; 7,336,763; 7,426,258; 7,563,026; 7,596,205; 7,608,834; 7,615,754; 7,629,587; 7,653,263; 8,378,310; 8,430,563; 9,180,215 and international patent application publication WO2015005891, each of which is incorporated herein by reference.

Current intraoral and extraoral digital dental x-ray system comprise an x-ray source with a milliamperes (mA) setting ranging in between 2.5 and 15 mA, a kilovolt peak (kVp) ranging in between 70 and 120 kVp and exposure times ranging in between 0.016-1.65 seconds for intraoral and up to 20 seconds for extraoral. PET uses small amounts of radioactive materials called radiotracers, a special camera and a computer to help evaluate organs and tissues functions. By identifying body changes at the cellular level, PET may detect the early onset of disease before it is evident on other imaging tests. PET scan includes gamma rays emitted by a positron-emitting radiotracer source, which is introduced into the body on a biologically active molecule. As the radiotracer undergoes positron emission decay, a pair of annihilation (gamma) photons moving in approximately opposite directions is produced. These are detected when they reach a scintillator in the scanning device, creating a burst of light which is detected by photomultiplier tubes or silicon avalanche photodiodes (Si APD). The raw data collected by a PET scanner represents near-simultaneous detection within a window of 1 to 12 nanoseconds of each other of annihilation photons by a pair of detectors. The PET scan takes 20-30 minutes depending on the area to be scanned. PET neuroimaging and cancer patient management has an effective radiation dose of 14 mSv. SPECT is similar to PET in its use of radioactive tracer material and detection of gamma rays. In contrast with PET, however, the tracers used in SPECT emit gamma radiation that is measured directly, and SPECT is able to provide true 3D information.

Recently, the milliamperes (mA) range has been taken into consideration in the attempts of reducing radiation dose to which dental patients are being exposed. The milliamperage is actually the units of the electrical current that is used to produce the radiation. The quantity, or number of x-rays emitted from the tube head, is controlled by the milliamperes. With all other technical factors (e.g., kVp, time) held constant, patient radiation dose is directly proportional to the milliamperes. A 50% in mA reduction results in a decrease in radiation dose by 50%. Radiation reduction in dentistry has been proposed through the introduction of a low-dose fluoroscopy technology by considerably minimizing the milliamperes settings and the use of image intensification as described in U.S. Pat. Nos. 6,543,936 and 8,430,563; and as described in international patent application publication WO2015005891. A major goal of the PET/SPECT studies is to obtain a good quality and detailed image of an object by the PET/SPECT scanner, and so it depends on how well the scanner detector performs in image formation in terms of QE.

These recent breakthroughs in dose reduction made possible the production of low milliamperes settings for dental use as disclosed in the '936 patent by using small image intensifiers in between a detector's converter/plate and collector. Despite these efforts, detector's configuration using the image intensifier and collector is still too bulky to be used inside the mouth and not ergonomic for the dentist to be placed extraorally while performing treatments on patients. Another disadvantage of intensifiers is image distortion originating from the projection of the x-ray image onto the curved input phosphor, and a smaller component corresponding to the mapping from the input phosphor to the output phosphor and the digital image matrix.

In order to overcome these obstacles, a current attempt of on-chip image intensification for low milliamperes image capturing is known from the '563 patent by amplifying the electrical signals within the detector's collecting area reducing a need for image intensifier coupling; however, in this approach no image collection description at the photocathode layer without passing through the wiring layer of the sensor is disclosed or suggested. As a result, this system would require a large pixel size ranging from 100 to 200 um.

A recent attempt described in WO2015005891 is believed to lead to increased low light collection efficiency. In this regard, a microlens array is incorporated in the detector for collecting and focusing light, which would have otherwise fallen onto the non-sensitive areas of the collector. The use of a microlens array in imaging detectors in between the converter/plate and the collector is believed to help increase image capture efficiency without compromising sensor's size and image resolution. It is also seen to be advantageous in that there is no necessity to couple or attach additional bulky components, as a microlens array generally is very thin and fits well within a detector. Microlens also contributes to system's pixel size reduction for an improved spatial resolution image.

Unfortunately, all of these approaches collect the light after going through the wiring layer and, as a result, the photocathode layer can only receive the remainder of the incoming light; the reflection reduces the signal that otherwise would be available for capture.

Thinned back illuminated sensors as disclosed in U.S. Pat. No. 4,266,334 are believed to have been invented around 1981. Back illuminated sensors currently are used in digital cameras and cell phones for capturing images in low light conditions, such as disclosed in U.S. Pat. No. 7,521,335.

In addition, the use of back-illuminated CMOS sensors has been suggested for x-ray astronomy imaging purposes in U.S. Pat. No. 8,575,559; for x-ray diffraction detection and radiation monitoring in U.S. Pat. No. 8,421,007; for medical computed tomography in U.S. Pat. Nos. 8,288,733, 8,121,248, 7,869,559, 7,620,143, 7,455,454, and 6,426,991; and for x-ray spectrometry purposes in U.S. Pat. No. 4,245,158.

On October, 2015, Uzbelger Feldman and Yang described a CMOS back illuminated sensor based prototype in terms of dose exposure and image resolution at the 66th Annual Session of the American Academy of Oral and Maxillofacial Radiology in Indianapolis, IN The back illuminated based x-ray imaging system reduced the dosage to half while keeping an 11 microns (um) pixel size, as compared to the microlens based system disclosed by Uzbelger Feldman et al. in 2013 and current available imaging technologies. In this investigation the converted light from a 0.1 mA and 70 kVp x-ray source at 0.04 seconds and continuous exposure times was collected at the photocathode layer without passing through the wiring layer of the sensor. This allowed a 90% fill factor and increased QE by the back illuminated approach as compared to the traditional front illuminated technology. Through the use of a back illuminated based system, radiation dosage was reduced in several orders of magnitude from the standard 7 mA to 0.1 mA with all other technical factors (e.g., kVp, time) held constant. In addition, a pixel size of 11 um would result in an increased system image spatial resolution as compared to the 18 um of digital intraoral radiography, 30 um of panoramic scanning, 76-100 um of CBCT scan, and 100-200 um of flat panel fluoroscopy.

As of today, none of the conventional intraoral and extraoral 2D and 3D dental modalities, digital tomosynthesis, photon-counting computed tomography, and PET/SPECT scan offer an x-ray imaging method and detector capable of increasing a detector's fill factor to light or QE after entering a detector's collection area without increasing pixel size. Consequently, low-dose x-ray imaging systems, methods, and apparatus in accordance with preferred embodiments of the invention are believed to be improvements in intraoral and extraoral 2D and 3D dental imaging, in digital tomosynthesis, in photon-counting computed tomography, and in PET/SPECT scans.

SUMMARY OF THE INVENTION

The present invention includes many aspects and features. Moreover, while many aspects and features relate to, and are described in, the context of dentistry, the present invention is not limited to use only in such context, as will become apparent from the following summaries and detailed descriptions of aspects, features, and one or more embodiments of the present invention.

In an aspect of the invention, a low-dose radiation imaging method comprises the steps of: (a) causing a beam to travel from an emitter through a patient examination area for receipt at a detector; and (b) within the detector, (i) transforming the beam that is received into light, (ii) collecting and converting the light into electrical signals representative of digital images corresponding to the patient examination area, including using a collector within the detector to collect the light as it passes to a photocathode layer of the collector without first passing through a wiring layer of the collector, and (iii) transmitting from the detector the data representative of digital images for display of the digital images to a user on a computing device.

In a feature of this aspect, the method further comprises aiming the light to the photosensitive areas of the collector within the detector, aiming the light away from non-photosensitive areas of the collector within the detector.

In a feature of this aspect, the method further comprises filtering the light at the detector.

In a feature of this aspect, a back illuminated sensor is used to convert the light into the electrical signals within the detector.

In a feature of this aspect, the method further comprises amplifying the electrical signals within the detector.

In various preferred embodiments with respect to this feature: the back illuminated sensor may comprise a charge coupled device (CCD), a complementary metal oxide semiconductor (CMOS), an active pixel sensor (APS) CMOS, an N-type metal-oxide-semiconductor (NMOS), an APS thin film transistor (TFT) or single-crystalline silicon nanomembrane (Si NM), or combination thereof; the back illuminated sensor comprises core material made of an organic material, an inorganic material, or combination thereof including Perovskite, halide Perovskite, lead halide Perovskite and single-crystalline Perovskite; the back illuminated sensor comprises a wiring layer oriented behind a photocathode layer; the back illuminated sensor comprises a radiation resistant chip or a non-radiation resistant chip; a wafer of the back illuminated sensor is stitched with one or more back illuminated sensor wafers thereby increasing the size of the back illuminated sensor; the back illuminated sensor comprises a rigid material, a flexible material, a curved material or a combination thereof; the back illuminated sensor has a pixel size from 0.01 microns to 500 microns; the back illuminated sensor comprises a thinned-back illuminated device, an electron multiplied device, an electron bombarded device, or combination thereof; and combinations thereof.

In a feature of this aspect, transforming the beam into light is performed by one or more organic x-ray converters, inorganic x-ray converters, or combination thereof including Perovskite, halide Perovskite, lead halide Perovskite and single-crystalline Perovskite. In various preferred embodiments with respect to this feature: the x-ray converter comprises a solid, liquid, gas, or combination thereof; a said x-ray converter is coupled to the collector; the x-ray converter is coupled to a plate and the plate is coupled to the collector; and combinations thereof.

In a feature of this aspect, the back illuminated collector acts as an x-ray converter, such as in a direct radiography approach.

In a feature of this aspect, the beam caused to be emitted comprises a low-dose gamma ray or X-ray beam.

In a feature of this aspect, the data is transmitted using an analog to digital converter.

In a feature of this aspect, the computing device is a desktop or laptop computer.

In a feature of this aspect, the computing device is a wireless mobile computing device.

In a feature of this aspect, the computing device is a tablet.

In a feature of this aspect, the computing device is a smartphone.

In a feature of this aspect, the method further comprises the steps of receiving the transmitted data and processing the data and displaying the digital images to a user on the computing device. In various preferred embodiments with respect to this feature: the digital images are displayed to a user as 2D and 3D still images; as real time video; or both; processing the data comprises reconstructing, noise filtering, recording, enhancing and freezing the digital data representative of digital images transmitted from the detector; processing the data comprises compiling a series of the digital images into a video having a video frame rate ranging from 1 to 10,000 frames per second; and combinations thereof. Furthermore, in respect to the foregoing, the method may include displaying digital images to a user as still images and in real time video, and data representative of a digital image may be transmitted to the mobile device at a video frame rate of 1 to 10,000 digital images per second.

In a feature of this aspect, the detector comprises a light proof housing within which components of the detector are enclosed. Such light proof housing further preferably comprises a radiation shielded back side in order to minimize backscattered radiation.

In a feature of this aspect, the detector is an intraoral or internal detector.

In a feature of this aspect, the detector is an extraoral or external detector.

In a feature of this aspect, the housing further comprises a coating layer that filters or reflects the light within the detector. The coating layer preferably is located on top of the converter.

In a feature of this aspect, the housing further contains a focusing arrangement that aims the light within the detector away from non-photosensitive areas of the collector and helps to reduce the quantity of scattered x-rays at the collector. The focusing arrangement preferably comprises a grid or microlens array.

In a feature of this aspect, the housing further contains an amplifier that amplifies the electrical signals within the detector.

In a feature of this aspect, the method is used in dental digital radiography; low-dose dental digital radiography; dental fluoroscopy; dental panoramic scanning; dental cephalometric scanning; dental cone beam computed tomography; linear tomography; digital tomosynthesis; dental x-ray stereoscopic spectroscopy; photon-counting computed tomography; positron emission tomography (PET); or single-photon emission computed tomography (SPECT).

In another aspect of the invention, a low-dose radiation imaging apparatus comprises: (a) one or more emitters each configured to emit a low-dose gamma or x-ray beam through a dental examination area; and (b) one or more detectors each configured to receive a said beam. Each detector comprises a housing containing: (i) a collector that converts the light into electrical signals representative of digital images corresponding to the patient examination area, wherein the light that is collected passes to a photocathode layer of the collector without passing through a wiring layer of the collector, and (ii) a transmitter that transmits from the detector the data representative of digital images for display of the digital images to a user on a computing device. The housing also preferably contains a converter that transforms the beam into light, or the collector may serve as the converter such as in a direct radiology approach.

In a feature of this aspect, the method further comprises rotating one or more emitters, one or more detectors, or combination thereof around the examination area using a rotational support and motor. Alternatively, one or more emitters, one or more detectors, or combination thereof are mounted to a wall or ceiling by appropriate mechanical arms, c-arms, u-arms or o-arm supports, such as being attached to a fixed gantry. Still yet, one or more emitters, detectors, or both may be handheld and portable in other alternatives.

In a feature, two or more emitters are configured to direct beams to the same detector.

In a feature of this aspect, the beam caused to be emitted comprises one or more intraoral or extraoral sources from the group of electromagnetic radiation, magnetic resonance, positron-emitting radionuclide, and a single-photon emission tracer.

In a feature of this aspect, the method is used in dental digital radiography; low-dose dental digital radiography; dental fluoroscopy; dental panoramic scanning; dental cephalometric scanning; dental cone beam computed tomography; linear tomography; digital tomosynthesis; dental x-ray stereoscopic spectroscopy; photon-counting computed tomography; positron emission tomography (PET); or single-photon emission computed tomography (SPECT).

In another aspect of the invention, an apparatus is configured to perform the imaging method of any of the foregoing aspects and features.

In another aspect, a detector for use in intraoral and extraoral 2D and 3D dental radiography and PET/SPECT comprises a converter and a collector, the detector configured to transform an x-ray beam into light and then convert the light into electrical signals at a photocathode layer of the collector without the light first passing through a wiring layer of the collector. In a feature of this aspect, the detector further comprises an amplifier and an analog-to-digital converter.

In another aspect of the invention, a method of making a back illuminated sensor comprises (a) flipping a silicon wafer of a conventional detector so as to orientate a wiring layer behind a photocathode layer of the wafer with respect to a direction of incident light to be received, and (b) thinning a side receiving the incident light so that the incident light strikes the photocathode layer of the wafer without passing through the wiring layer of the wafer.

Another aspect of the invention comprises a low-dose radiation imaging method as disclosed herein.

Another aspect of the invention comprises a low-dose radiation imaging apparatus as disclosed herein.

Another aspect of the invention comprises a low-dose radiation imaging system as disclosed herein.

Still additional aspects, features, and embodiments of the invention are disclosed in the incorporated provisional patent application, to which priority is claimed.

In addition to the aforementioned aspects and features of the present invention, it should be noted that the present invention further encompasses the various possible combinations and subcombinations of such aspects and features. Thus, for example, claims in this or a divisional or continuing patent application or applications may be separately directed to any aspect, feature, or embodiment disclosed herein, or combination thereof without requiring any other aspect, feature, or embodiment.

BRIEF DESCRIPTION OF THE DRAWINGS

One or more preferred embodiments of the present invention now will be described in detail with reference to the accompanying drawings.

DETAILED DESCRIPTION

Figure 1B:
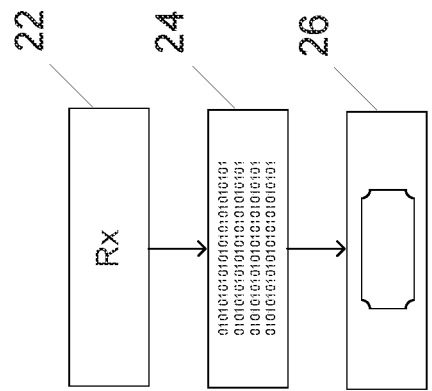
FIG. 1B is a schematic illustration of steps of a method performed by a computing device in imaging apparatus and methods in accordance with a preferred embodiment of the invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability in the United States of 35 U.S.C. § 112(f) with regard to claim construction, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, as used herein "low-dose" in the context of x-rays and gamma rays is intended to mean "an x-ray or gamma ray beam comprising a low milliamperes setting below the conventional dental imaging standard of 2.5 to 15 milliamperes."

Referring now to the drawings, one or more preferred embodiments of the present invention are next described. The following description of one or more preferred embodiments is merely exemplary in nature and is in no way intended to limit the invention, its implementations, or uses.

Figure 1A:
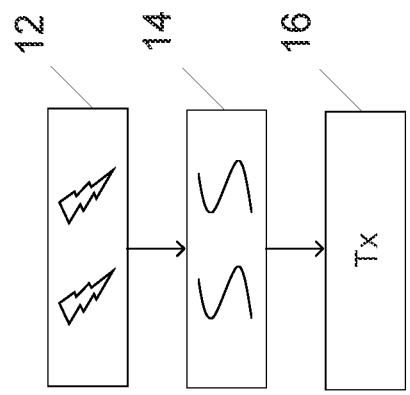
FIG. 1A is a schematic illustration of steps of a method performed by a detector in imaging apparatus and methods in accordance with a preferred embodiment of the invention.
Figure 1:
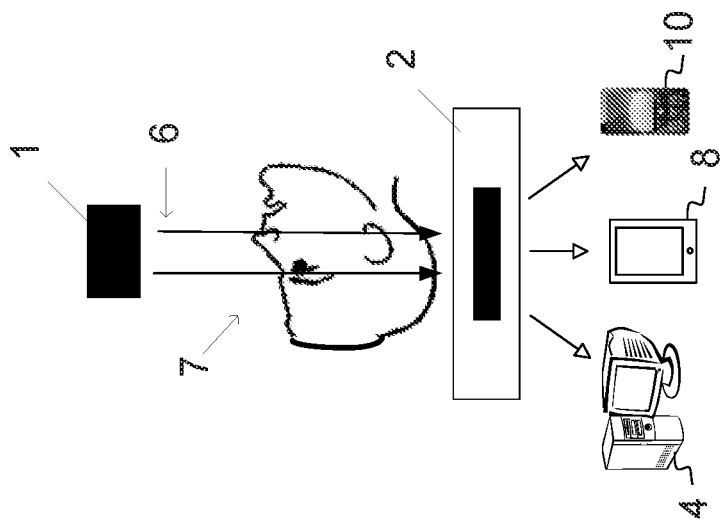
FIG. 1 is a schematic illustration of imaging apparatus and methods in accordance with a preferred embodiment of the invention.

Turning now to FIG. 1, a schematic illustration of imaging apparatus and methods in accordance with a preferred embodiment of the invention is described. In this respect, a back illuminated sensor preferably is included as a collector component of a detector 2 for use in intraoral and extraoral 2D and 3D dental radiography, digital tomosynthesis, photon-counting computed tomography and PET/SPECT. Specifically, an emitter 1 produces a beam 6 that travels through a patient examination area 7 and that is received at the detector 2. The beam 6 emitted comprises gamma radiation or x-rays (both of which are generally referred to herein simply as x-rays). The detector 2 is shown in FIG. 1 as an extraoral or external detector.

As schematically represented in FIG. 1A, certain steps preferably are performed within the detector 2, including a step 12 of transforming the beam 6 that is received at the detector 2 into light using a converter; a step 14 of capturing and amplifying electric signals using a collector within the detector to collect the light as it passes to a photocathode layer of the collector without first passing through a wiring layer of the collector, and to convert the light into electrical signals representative of digital images corresponding to the patient examination area 7; and a step 16 of transmitting from the detector 2, based on the electric signals, data representative of digital images for display of digital images to a user on a computing device. The detector 2 is further discussed in greater detail below with reference to FIG. 3.

Computing devices of users are schematically shown in FIG. 1 as including a desktop or laptop computer 4, a tablet 8, and a smartphone 10. The transmission of the data that is performed at step 16 within the detector preferably is received by such a computing device. Specifically, FIG. 1B schematically shows certain steps preferably performed within such a computing device, including the step 22 of receiving at such computing device the data transmitted from the detector 2 at step 16; the step 24 of processing, noise filtering, reconstructing, and enhancing the received data; and the step 26 of displaying the 2D or 3D digital images to a user on a display of the computing device.

Figure 2:
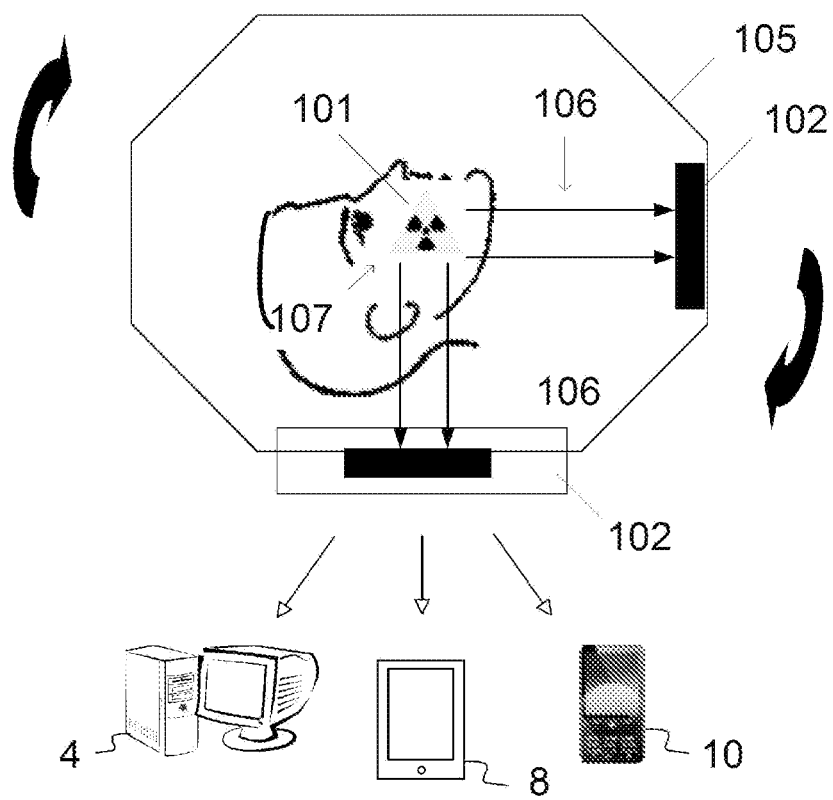
FIG. 2 is a schematic illustration of imaging apparatus and methods in accordance with a preferred embodiment of the invention.

FIG. 2 is a schematic illustration of imaging apparatus and methods similar to the illustration of FIG. 1, but in which a back illuminated sensor preferably is included as a collector component in each of two or more detectors 102 for use in photon-counting computed tomography, PET and SPECT in the dental context and digital tomosynthesis. Furthermore, each detector 102 is shown as being mounted on a common support 105 for rotational movement around the patient examination area 107. The emitter 101 is shown in FIG. 2 as being an intraoral or internal source inside of the patient (including, for example, a positron-emitting radiotracer source, or a single-photon emission tracer) as emitting radiation 106.

It will be appreciated that while detector 2 and detectors 102 have been shown as extraoral or external detectors in the disclosed embodiments of FIGS. 1 and 2, intraoral or internal detectors can be used in other embodiments of the invention. In any such instance, any detector used preferably includes a collector in which the light is collected at a photocathode layer without passing through a wiring layer. In accordance therewith, the light preferably is collected using a back illuminated sensor such that in the detector beam 206 is converted into light and then focused, filtered, and collected at a photocathode layer without passing through the wiring layer.

Figure 3:
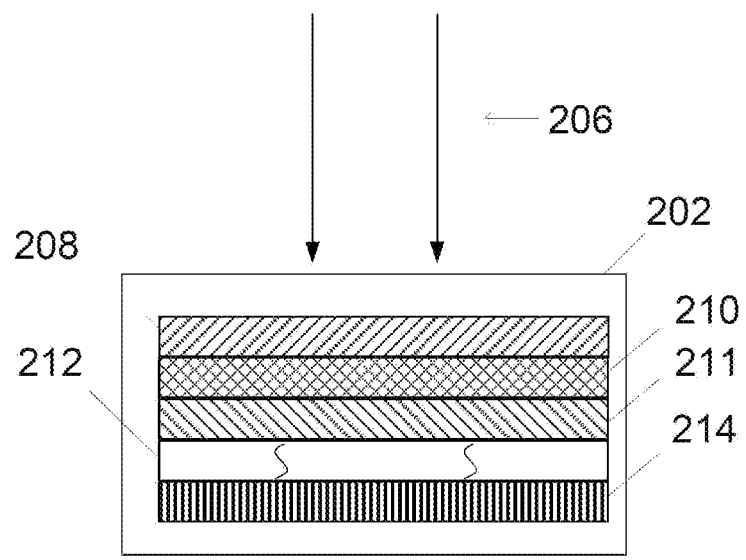
FIG. 3 is a schematic illustration of a detector in imaging apparatus and methods in accordance with a preferred embodiment of the invention.

FIG. 3 is a schematic illustration of a detector used in imaging apparatus and methods in accordance with a preferred embodiment of the invention. The direction of travel of beam 206 comprising low-dose gamma rays or X-rays for detection by the detector is indicated by the arrows in FIG. 3. As shown in FIG. 3, the detector comprises a housing 202 in which is contained and enclosed a coating layer 208, a converter 210, a focusing arrangement 211 (including, for example, a grid), a collector 212, and a transmitter 214. The focusing arrangement 211 preferably comprises a microlens array.

Figure 4:
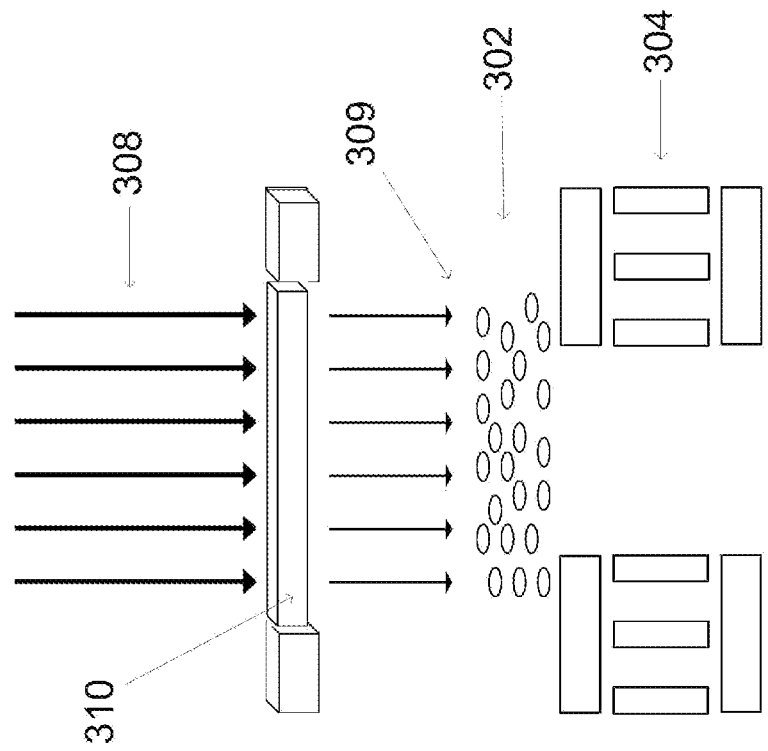
FIG. 4 is a schematic illustration of a front illuminated architecture including a wiring layer and photocathode layer in a conventional sensor.
Figure 5:
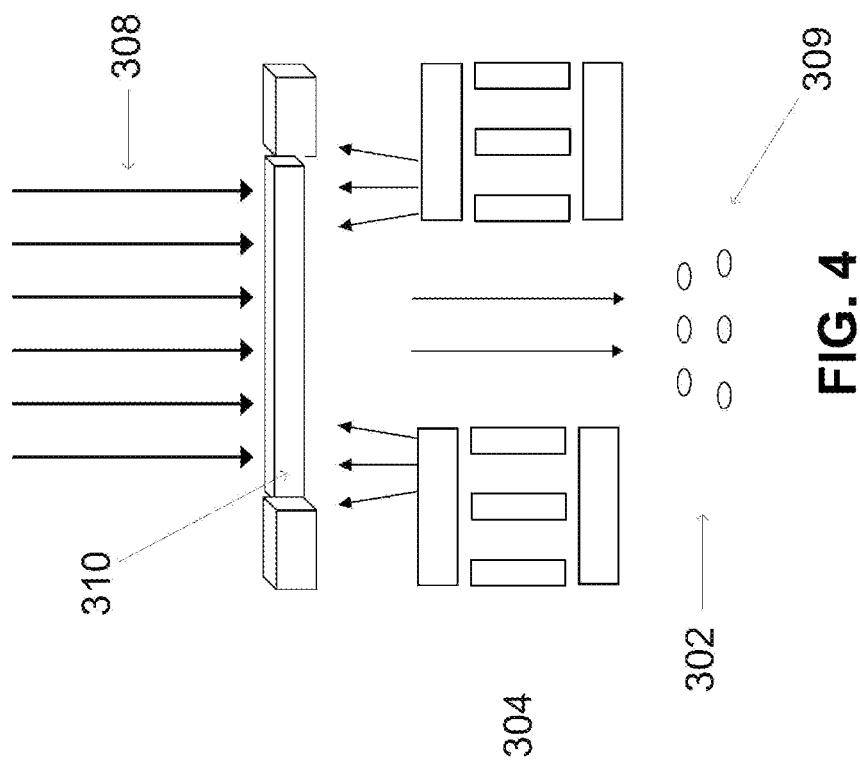
FIG. 5 is a schematic illustration of a back illuminated architecture including a wiring layer and photocathode layer as found in preferred embodiments of the invention.

The collector 212 preferably includes a back illuminated sensor. In this regard, FIG. 4 schematically illustrates a front illuminated architecture including a wiring layer 304 and photocathode layer 302 in a conventional sensor, and for comparison FIG. 5 illustrates a back illuminated architecture including a wiring layer 304 and photocathode layer 302 as found in preferred embodiments of the invention. As seen in FIG. 4, light is collected at area 309 behind wiring layer 304 relative to the direction of travel of light 308 through pixel gate 310, whereas in FIG. 5, light is collected at area 309 before wiring layer 304 relative to the direction of travel of the light 308 through the pixel gate 310.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. For example, one or more of the emitters and detectors may be mounted to a wall or ceiling by appropriate supports, or may be handheld and portable. Rotational support apparatus for the emitters and detectors also may be provided as disclosed, for example, in incorporated references, such as U.S. Pat. No. 8,430,563.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. An imaging method, comprising the steps of:
   (a) causing a radiation beam to travel from an emitter through an examination area for receipt at a detector;
   (b) using a converter within the detector, transforming the radiation beam that is received into light;
   (c) using a collector within the detector, transforming the light into electrical signals representative of digital images corresponding to the examination area, the collector comprising photosensitive areas and a wiring layer, wherein the collector is oriented and configured such that, relative to a direction of travel of the light, the photosensitive areas are located in front of the wiring layer, whereby that the light encounters the photosensitive areas without first passing through the wiring layer; and (d) using a transmitter within the detector, transmitting from the detector based on the electrical signals data representative of digital images for display of the digital images on a computing device.

2. The imaging method of claim 1, wherein the method further comprises noise filtering the data representative of digital images.

3. The imaging method of claim 1, wherein the detector comprises a pixel gate and has a pixel size from 0.01 microns to 500 microns.

4. The imaging method of claim 1, wherein the method further comprises compiling, based on the data, a series of digital images into a video having a video frame rate ranging from 1 to 10,000 frames per second.

5. The imaging method of claim 1, wherein the detector is an intraoral or internal detector.

6. The imaging method of claim 1, wherein the detector is an extraoral or external detector.

7. The imaging method of claim 1, wherein the beam caused to be emitted comprises one or more intraoral or extraoral sources from the group of electromagnetic radiation, magnetic resonance, positron-emitting radionuclide, and single-photon emission tracer.

8. The imaging method of claim 1, further comprising rotating the emitter, the detector, or both around the examination area using a rotational support and motor.

9. The imaging method of claim 1, wherein the data is transmitted using analog to digital converters.

10. The imaging method of claim 1, wherein the emitter, the detector, or both, are mounted to a wall or ceiling by appropriate supports, or are handheld or portable.

11. An imaging method, comprising the steps of:
(a) causing a radiation beam to travel from an emitter through an examination area for receipt at a detector;
(b) transforming the radiation beam that is received by the detector into light;
(c) transforming the light within the detector into electrical signals representative of digital images corresponding to the examination area, the detector comprising photosensitive areas for transforming the light and at least one wiring layer, wherein the light encounters the photosensitive areas without first passing through any said wiring layer of the detector; and
(d) transmitting from the detector based on the electrical signals data representative of digital images of the examination area for display of the digital images on a computing device.

12. The imaging method of claim 11, wherein the method further comprises noise filtering the data representative of digital images.

13. The imaging method of claim 11, wherein the detector comprises a pixel gate and has a pixel size from 0.01 microns to 500 microns.

14. The imaging method of claim 11, wherein the method further comprises compiling, based on the data, a series of digital images into a video having a video frame rate ranging from 1 to 10,000 frames per second.

15. The imaging method of claim 11, wherein the detector is an intraoral or internal detector.

16. The imaging method of claim 11, wherein the detector is an extraoral or external detector.

17. The imaging method of claim 11, wherein the beam caused to be emitted comprises one or more intraoral or extraoral sources from the group of electromagnetic radiation, magnetic resonance, positron-emitting radionuclide, and single-photon emission tracer.

18. The imaging method of claim 11, further comprising rotating the emitter, the detector, or both around the examination area using a rotational support and motor.

19. The imaging method of claim 11, wherein the data is transmitted using analog to digital converters.

20. The imaging method of claim 11, wherein the emitter, the detector, or both, are mounted to a wall or ceiling by appropriate supports, or are handheld or portable.

* * * * *